(12) United States Patent
Gou et al.

(10) Patent No.: US 11,007,196 B1
(45) Date of Patent: May 18, 2021

(54) METHOD FOR PREPARING COMPOSITION OF MATTER COMPRISING FLUOROURACIL AND ZINC-MERCURY-SELENIUM QUANTUM DOT

(71) Applicant: Ningxia Medical University, Yinchuan (CN)

(72) Inventors: Guojing Gou, Yinchuan (CN); Xueqin Jin, Yinchuan (CN); Rui Wang, Yinchuan (CN); Qinyu Pei, Yinchuan (CN); Huiqin Yao, Yinchuan (CN); Yumei Zhang, Yinchuan (CN); Lingxia Zuo, Yinchuan (CN)

(73) Assignee: NINGXIA MEDICAL UNIVERSITY, Yinchuan (CN)

( * ) Notice: Subject to any disclaimer, the term of this patent is extended or adjusted under 35 U.S.C. 154(b) by 0 days.

(21) Appl. No.: 16/844,037

(22) Filed: Apr. 9, 2020

(51) Int. Cl.
*A61K 31/513* (2006.01)
*C09K 11/89* (2006.01)
(Continued)

(52) U.S. Cl.
CPC .......... *A61K 31/513* (2013.01); *A61K 9/1611* (2013.01); *A61K 9/1652* (2013.01);
(Continued)

(58) Field of Classification Search
CPC .. A61K 31/513; A61K 9/1652; A61K 9/1682; A61K 9/1611; C09K 11/892; B82Y 5/00; B82Y 15/00
See application file for complete search history.

(56) References Cited

FOREIGN PATENT DOCUMENTS

EP          236896481     *   9/2011

OTHER PUBLICATIONS

Schneider et al, Hydrothermal Routes for the Synthesis of CdSe Core Quantum Dots, Nanotechnology and Nanomaterials: State of the Art of Quantum Dot System Fabrication, InTech, pp. 119-140. (Year: 2012).*

* cited by examiner

*Primary Examiner* — Carlos A Azpuru
(74) *Attorney, Agent, or Firm* — Matthias Scholl P.C.; Matthias Scholl (57) ABSTRACT

A method for preparing a composition of matter, the method including: 1) mixing a $Zn(NO_3)_2$ solution, a $Hg(NO_3)_2$ solution, and a mercaptopropionic acid solution, thereby yielding a precursor solution of $Zn^{2+}$—$Hg^{2+}$-mercaptopropionic acid; dissolving a selenium powder and a $NaBH_4$ solid in water thereby yielding a NaHSe slurry; mixing the precursor solution and the NaHSe slurry thereby yielding zinc-mercury-selenium (ZnHgSe) quantum dot; 2) preparing a drug delivery system including dextran-magnetic layered double hydroxide-fluorouracil (DMF); binding the drug delivery system and the ZnHgSe quantum dot in a mass ratio of 1:1-3; and grinding the drug delivery system including the ZnHgSe quantum dot (QD) thereby yielding powders; and 3) dissolving the powders in absolute ethyl alcohol thereby yielding a first suspension; ultrasonically dispersing the first suspension thereby yielding a second suspension, magnetically separating the second suspension thereby yielding a solid product, centrifuging and washing the solid product.

6 Claims, 9 Drawing Sheets

(51) Int. Cl.
 *A61K 9/16* (2006.01)
 *B82Y 15/00* (2011.01)
 *B82Y 5/00* (2011.01)

(52) U.S. Cl.
 CPC .......... *A61K 9/1682* (2013.01); *C09K 11/892* (2013.01); *B82Y 5/00* (2013.01); *B82Y 15/00* (2013.01)

METHOD FOR PREPARING COMPOSITION OF MATTER COMPRISING FLUOROURACIL AND ZINC-MERCURY-SELENIUM QUANTUM DOT

BACKGROUND

The disclosure relates to a method for preparing a composition of matter comprising dextran-magnetic layered double hydroxide-fluorouracil and zinc-mercury-selenium quantum dot.

At present, there are few studies on the mechanism of cancer cell death induced by chemotherapy agents. A key technical bottleneck is the dearth of biological probes for elucidating the mechanism of action and for marking the changes of the morphological structure of cancer cells.

SUMMARY

The disclosure provides a method for preparing a composition of matter, the method comprising:

a) dissolving $Zn(NO_3)_2$ in water thereby yield a $Zn(NO_3)_2$ solution, clarifying the $Zn(NO_3)_2$ solution, and introducing nitrogen to the $Zn(NO_3)_2$ solution and magnetically stirring to remove oxygen at room temperature; adding $Hg(NO_3)_2$ solution to the $Zn(NO_3)_2$ solution in a molar ratio of $Zn^{2+}/Hg^{2+}=1:0.03-0.06$ thereby yielding a mixture; dispersing the mixture thereby yielding a dispersion, and adding a mercaptopropionic acid solution to the dispersion in a molar ratio of $Zn^{2+}$/mercaptopropionic acid=1:1.6-2.0; and adjusting a pH of the dispersion comprising the mercaptopropionic acid to 6.0-9.0 thereby yielding a precursor solution of $Zn^{2+}$—$Hg^{2+}$-mercaptopropionic acid;

b) dissolving a selenium (Se) powder and a $NaBH_4$ solid in a molar ratio of $Se/NaBH_4=1:1.5-2.5$ in water; magnetically stirring a mixture of the selenium powder and the $NaBH_4$ solid at a constant temperature of 40-50° C. under nitrogen protection until the selenium powder disappears, thereby yielding a NaHSe slurry;

c) mixing the precursor solution of $Zn^{2+}$—$Hg^{2+}$-mercaptopropionic acid and the NaHSe slurry in a molar ratio $Zn^{2+}/NaHSe=1:0.125-1$; magnetically stirring a resulting mixed slurry at a constant temperature of 80-100° C. under nitrogen protection;

d) aging the mixed slurry; adding ethanol to the mixed slurry thereby yielding a supernatant and a precipitate discarding the supernatant, and centrifuging the precipitate to obtain a solid-phase sample; washing the solid-phase sample with absolute ethanol and drying under vacuum, thereby yielding a zinc-mercury-selenium (ZnHgSe) quantum dot;

e) preparing a drug delivery system comprising dextran-magnetic layered double hydroxide-fluorouracil (DMF); binding the drug delivery system and the ZnHgSe quantum dot in a mass ratio of 1:1-3; and grinding a mixture of the drug delivery system and the ZnHgSe quantum dot (QD) thereby yielding powders; and f) dissolving the powders obtained in e) in absolute ethyl alcohol thereby yielding a first suspension; ultrasonically dispersing the first suspension thereby yielding a second suspension, magnetically separating the second suspension thereby yielding a solid product, centrifuging and washing the solid product using absolute ethyl alcohol, and vacuum drying.

In a), magnetically stirring the solution to remove oxygen is implemented for 30-40 min; the mercaptopropionic acid solution is mixed with the dispersion for 30-60 min, and the pH of the dispersion comprising the mercaptopropionic acid is adjusted to 6.0-9.0 using a 2.0 $mol \times L^{-1}$ NaOH solution.

In d), the mixed slurry is aged for 40-80 min; the solid-phase sample is washed with absolute ethanol for 2-3 times; the precipitate is centrifuged at 4000-5000 rpm at approximately 20° C.; the solid-phase sample is dried at 65-80° C. under 0.085 megapascal; and in a) and c), the magnetic stirring is performed at 200-300 rpm.

In f), the suspension is ultrasonically dispersed in a 30-50° C. water bath for 1-3 hours.

In f). the solid product is washed using absolute ethyl alcohol for 2-3 times.

In f). the solid product is dried at 50-60° C. under 0.085 megapascal.

The composition of matter is a magnetic layered fluorescent nanoparticle. The dextran-magnetic layered double hydroxide-fluorouracil is a sustained release drug delivery system, and the water-soluble near-infrared ZnHgSe quantum dot is used as a fluorescent tracer. The nanoparticle is formed by electrostatic binding technology, and can induce the nuclear explosion of cancer cells.

DMF in the DMF-QD nanoparticles can trigger the swelling and death of cancer cells, causing cell swelling and increasing the membrane permeability of the cells at the early stage. The continuous invasion of a large number of DMF particles causes different degrees of damage to organelles; the swelling and explosion of the leads to cell disintegration. Quantum dots can mark the complete process of DMF particles invading organelles and inducing cell swelling, and can strengthen the explosion energy and destruction effect of the cell nucleus and cell membranes.

The disclosure can detect the swelling and death of cancer cells by using in situ imaging technology and MTT experiment. The technical conditions and operation process of live cell imaging are as follows:

digesting human gastric cancer MGC-803 cells in exponential phase with trypsin, and centrifuging the digested cells to make a single cell suspension; inoculating the single cells in a special culture dish for laser confocal imaging (inoculation number 20×10⁴), and then incubating in an incubator of 37° C. and 5% $CO_2$ for 24 h; using RPMI 1640 medium containing 10% fetal bovine serum to prepare ZnHgSe quantum dots at 0.6 $mg \cdot mL^{-1}$, DMF at 1.1 $mg \cdot mL^{-1}$, and DMF-QD complex solution at 1.0 to 1.6 $mg \cdot mL^{-1}$; and storing the prepared solutions in a refrigerator at 4° C.; culturing the cells for 24 h until the cells adhere to the wall of the culture dish; discarding the supernatant of the culture medium in each well and washing the cells with PBS 3 times; after adding 0.5 mL of culture medium to the culture dish, transferring the culture dish into the live cell workstation via a transfer window; setting the working conditions of the live cell workstation (i.e. at 37° C. and 5% $CO_2$); aspirating the culture medium by a disposable pipette, and then adding 2 mL of the prepared drug solution to the culture dish; setting the parameters of transmission channel and fluorescence channel prior to photographing, in which the fluorescence channel is a 575±25 nm laser with a light intensity of 32% and transmission channel is a 632±60 nm bandpass filter with a light intensity of 2%; continuously photographing the cells for 9 h, and automatically photographing every 2 min.

DETAIL DESCRIPTION OF EMBODIMENTS

Example 1

Preparation of Dextran-Magnetic Layered Double Hydroxide-Fluorouracil (DMF) and ZnHgSe Quantum Dot with a Mass Ratio of 1:3.

(1) Synthesis of Water-Soluble Near-Infrared ZnHgSe Quantum Dot by One-Pot Synthesis in Aqueous Phase.

0.5131 g of $Zn(NO_3)_2 \cdot 4H_2O$ solids were weighed and put into a 1000 mL reactor. 900 mL of distilled water was added to dissolve the solids to form a clarified solution. The oxygen was removed with magnetic stirring at 300 rpm for 30 min under nitrogen protection at room temperature. 863 μL of $Hg(NO_3)_2 \cdot 4H_2O$ solution was added in a molar ratio of $Zn^{2+}/Hg^{2+}=1:0.05$ to the clarified solution, and the mixture was dispersed uniformly into a dispersion. 22 μL of mercaptopropionic acid (MPA) solution was added in a molar ratio of $Zn^{2+}/MPA=1:1.8$ to the dispersion, followed by a 50 min in-situ reaction. And then the pH was adjusted to 8.5 to prepare a precursor solution of $Zn^{2+}$—$Hg^{2+}$-MPA.

0.017 g of selenium powder and 0.016 g of $NaBH_4$ solids were weighed according to the molar ratio of $Se/NaBH_4=1:2$, and the mixed solids were put into a 100 mL reactor. 10 mL of distilled water was added to dissolve the solids to form a mixture. The mixture was magnetic stirred at 300 rpm at a constant temperature of 45° C. under nitrogen protection until selenium powder disappeared to yield NaHSe slurry.

The NaHSe hot slurry prepared in b) was added in a molar ratio $Zn^{2+}/NaHSe=1:0.125$ to the precursor solution of $Zn^{2+}$—$Hg^{2+}$-MPA prepared in a). The mixed slurry was magnetic stirred at 300 rpm at a constant temperature of 100° C. under nitrogen protection until fluorescence intensity of the liquid phase no longer increases.

The stirred slurry was aged under static conditions for 60 min. Ethanol was added and allowed to settle and separate completely. The supernatant was aspirated and discarded, and the precipitate was centrifuged at 500 rpm at room temperature to obtain a solid-phase sample. The obtained solid-phase sample was washed with absolute ethanol 2-3 times and then dried in a vacuum dryer at 65° C. and 0.085 MPa.

(2) Preparation of DMF-QD Nanoparticles:

6 mg of water-soluble near-infrared ZnHgSe quantum dots and 2 mg of DMF solid-phase sample were weighed and put into an agate mortar, followed by mixing and grinding for 10-50 min to obtain a mixed powder. The mixed powder was suspended and dispersed with absolute ethanol, and the suspension was placed in a water bath at 45° C. and ultrasonically dispersed for 70 min. The magnetic solid substance in the liquid-phase was attracted to a magnet, and the liquid-phase was discarded. Once more the magnetic solid substance was repeated the processes of dispersing, ultrasonic and magnetic separation. Then the separated solid was centrifuged at 5000 rpm at room temperature, and the solid-phase was washed with absolute ethanol 2-3 times and dried in a vacuum dryer at 50-60° C. and 0.085 MPa, thus yielding the final sample.

(3) Phase Analysis of Synthetic Samples and Characterization of Physicochemical Properties Thereof:

XRD spectrum of the samples was detected by a Rigaku D/max-rB XRD-6000 Diffractometer (Cu Kα, λ=0.15406 nm) at 40 kV and 30 mA. IR spectrum (KBr tablet, 4000 $cm^{-1}$ to 400 $cm^{-1}$) of the samples was detected by a TENEOR27 Infrared Spectrometer (Bruker, Germany). Thermal analysis of the samples was detected by a SETSYS-1750 CS Thermal Analyzer (SETARAM, France) ($N_2$ atmosphere, heating rate 10° C. $\cdot min^{-1}$, 30-650° C. Morphology of the particles was characterized by Transmission Electron Microscopy (Hitachi H-7560B), and the method comprises the following steps: the samples were dissolved with ultrapure water; several drops of suspension was then added on a copper mesh and the air was kept dry enough; morphology of nanoparticle was observed and photographed under the conditions of an acceleration voltage of 80 kV and a magnification of 50,000 to 70,000 times. Zeta potential of the samples was measured with a Malvern Laser Particle Size Analyzer, and the method comprises: 1 mL of ultrapure water (containing the samples at a concentration equal to or larger than 0.5 $g \cdot L^{-1}$) was added to the special cuvette for measuring zeta potential; the same sample was measured three times.

Example 2

Preparation of DMF-QD nanoparticle with a mass ratio of 1:2, and 1.4 mg/μL of the DMF-QD nanoparticles was applied to the human gastric cancer MGC-803 cell. The live cell imaging was observed.

(1) Synthesis of Water-Soluble Near-Infrared ZnHgSe Quantum Dot:

5.1313 g of $Zn(NO_3)_2 \cdot 4H_2O$ solids were weighed and put into a 1000 mL reactor. 900 mL of distilled water was added to dissolve the solids to form a clarified solution. The oxygen was removed with magnetic stirring at 300 rpm for 30 min under nitrogen protection at room temperature. 8.6 mL of $Hg(NO_3)_2 \cdot 4H_2O$ solution having a concentration of 0.01 $mol \cdot L^{-1}$ was added to the clarified solution, and the mixture was dispersed uniformly for 30 min into a dispersion. 0.22 mL of mercaptopropionic acid (MPA) solution was added to the dispersion, followed by a 50 min in-situ reaction. After then the pH was adjusted with NaOH solution having a concentration of 2.0 $mol \cdot L^{-1}$ to 9.0 to prepare a precursor solution of $Zn^{2+}$—$Hg^{2+}$-MPA.

0.17 g of selenium powder and 0.16 g of $NaBH_4$ solids were weighed, and the mixed solids were put into a 100 mL reactor. 10 mL of distilled water was added to dissolve the solids to form a mixture. The mixture was magnetic stirred at 300 rpm at a constant temperature of 45° C. under nitrogen protection until selenium powder disappeared to yield NaHSe slurry. The NaHSe slurry was added to the precursor solution of $Zn^{2+}$—$Hg^{2+}$-MPA, and magnetic stirred at 300 rpm at a constant temperature of 100° C. under nitrogen protection until fluorescence intensity of the liquid phase no longer increases. The stirred slurry was aged under static conditions for 60 min. And ethanol was added and allowed to settle and separate completely. The supernatant was aspirated and discarded, and the precipitate was centrifuged at 500 rpm at room temperature to obtain a solid-phase sample. The obtained solid-phase sample was washed with absolute ethanol 2-3 times and then dried in a vacuum dryer at 65° C. and 0.085 MPa.

(2) Preparation of DMF-QD Nanoparticles:

0.06 g of water-soluble near-infrared ZnHgSe quantum dots and 0.03 g of DMF solid-phase sample were weighed and put into an agate mortar, followed by mixing and grinding for 10-50 min to obtain a mixed powder. The mixed powder was suspended and dispersed with absolute ethanol, and the suspension was placed in a water bath at 45° C. and ultrasonically dispersed for 70 min. The magnetic solid substance in the liquid-phase was attracted to a magnet, and the liquid-phase was discarded. Once more the magnetic solid substance was repeated the processes of dispersing, ultrasonic and magnetic separation. Then the separated solid was centrifuged at 5000 rpm at room temperature, and the solid-phase was washed with absolute ethanol 2-3 times and dried in a vacuum dryer at 50-60° C. and 0.085 MPa, thus yielding the final sample.

(3) DMF-QD nanoparticles having a concentration of 1.4 mg/μL applied to human gastric cancer MGC-803 cells, and the nuclear explosion and swelling of cancer cells were observed with a live cell workstation:

Human gastric cancer MGC-803 cells in exponential phase were digested with trypsin, and the digested cells were centrifuged to make a single cell suspension; the single cells were inoculated in a special culture dish for laser confocal imaging (inoculation number $20 \times 10^4$), and then incubated in an incubator of 37° C. and 5% $CO_2$ for 24 h; RPMI 1640 medium containing 10% fetal bovine serum was used to prepare ZnHgSe quantum dots at 0.6 mg·$mL^1$, DMF at 1.1 mg·$mL^{-1}$, and DMF-QD complex solution at 1.0 to 1.6 mg·$mL^{-1}$; and the prepared solutions were stored in a refrigerator at 4° C. for future use; the cells were cultured for 24 h until the cells adhered to the wall of the culture dish; the supernatant of the culture medium in each well was discarded and the cells were washed with PBS 3 times; after addition of 0.5 mL of culture medium, the culture dish was transferred into the live cell workstation via a transfer window; the working conditions of the live cell workstation was set to 37° C. and 5% $CO_2$; the culture medium was aspirated by a disposable pipette, and then 2 mL of the prepared drug solution was added to the culture dish; the parameters of transmission channel and fluorescence channel was set prior to photographing, in which the fluorescence channel was a 575±25 nm laser with a light intensity of 32% and transmission channel was a 632±60 nm bandpass filter with a light intensity of 2%; continuously photographed the cells for 9 h, and automatically photographed every 2 min.

Example 3

Preparation of magnetic layered fluorescent DMF-QD nanoparticle with a mass ratio of 1:1; the DMF-QD nanoparticles having a concentration of 1.2 mg/μL was applied to human gastric cancer MGC-803 cell to perform live cell imaging; and the ability to kill cancer cells of the DMF-QD nanoparticle in vitro was evaluated by MTT method.

(1) Synthesis of Water-Soluble Near-Infrared ZnHgSe Quantum Dot:

a. 0.5131 g of $Zn(NO_3)_2 \cdot 6H_2O$ solids were weighed and put into a 1000 mL reactor. 900 mL of distilled water was added to dissolve the solids to form a clarified solution. The oxygen was removed with magnetic stirring at 300 rpm for 30 min under nitrogen protection at room temperature. 862.5 μL of $Hg(NO_3)_2 \cdot 4H_2O$ solution was added in a molar ratio of $Zn^{2+}/Hg^{2+}=1:0.05$ to the clarified solution, and the mixture was dispersed uniformly into a dispersion. 21.5 μL of mercaptopropionic acid (MPA) solution was added in a molar ratio of $Zn^{2+}/MPA=1:1.8$ to the dispersion, followed by a 50 min in-situ reaction. And then the pH was adjusted with NaOH solution having a concentration of 2.0 mol·$L^{-1}$ to 8.5 to prepare a precursor solution of $Zn^{2+}$—$Hg^{2+}$-MPA.

b. 0.017 g of selenium powder and 0.016 g of $NaBH_4$ solids were weighed and the mixed solids were put into a 100 mL reactor. 10 mL of distilled water was added to dissolve the solids to form a mixture. The mixture was magnetic stirred at 300 rpm at a constant temperature of 45° C. under nitrogen protection until selenium powder disappeared to yield NaHSe slurry;

c. the NaHSe hot slurry prepared in b) was added to the precursor solution of $Zn^{2+}$—$Hg^{2+}$-MPA prepared in a). The mixed slurry was magnetic stirred at 300 rpm at a constant temperature of 100° C. under nitrogen protection until fluorescence intensity of the liquid phase no longer increases;

d. the stirred slurry was aged under static conditions for 60 min. Ethanol was added and allowed to settle and separate completely. The supernatant was aspirated and discarded, and the precipitate was centrifuged at 500 rpm at room temperature to obtain a solid-phase sample. The obtained solid-phase sample was washed with absolute ethanol 2-3 times and then dried in a vacuum dryer at 65° C. and 0.085 MPa.

(2) Preparation of Magnetic Layered Fluorescent DMF-QD Nanoparticles by Ultrasonic Dispersion and Electrostatic Binding Technology:

a. water-soluble near-infrared ZnHgSe quantum dots and DMF nano-drugs were weighed in a mass ratio of 1:1 and put into an agate mortar, followed by mixing and grinding for 30 min to obtain a mixed powder;

b. The mixed powder was suspended and dispersed with absolute ethanol, and the suspension was placed in a water bath at 40° C. and ultrasonically dispersed for 3 h.

c. The magnetic solid substance in the liquid-phase was attracted to a magnet, and the liquid-phase was discarded. Once more the magnetic solid substance was repeated the processes of dispersing, ultrasonic and magnetic separation. Then the separated solid was centrifuged at 5000 rpm at room temperature, and the solid-phase was washed with absolute ethanol 2-3 times and dried in a vacuum dryer at 50-60° C. and 0.085 MPa, thus yielding the final sample.

(3) DMF-QD nanoparticles having a concentration of 1.2 mg/μL was applied to human gastric cancer MGC-803 cells, and the nuclear explosion and swelling of cancer cells were observed with a live cell workstation:

Conditions and operation procedures were the same as that in (3) of Example 2, except the concentration of the drug.

(4) Evaluation of Effect of DMF-QD Nanoparticle on Cancer Cells by MTT Experiment:

Pharmaceutical reagents were divided into four groups including ZnHgSe quantum dot group, DMF group, DMF-QD group and blank control group. Human gastric cancer MGC-803 cells in exponential phase were digested with trypsin, followed by addition of medium containing 10% fetal bovine serum to make a single cell suspension. The cells were seeded in a 96-well cell culture plate (100 μL of cell suspension was added to each well, containing $9 \times 10^3$ cells) and cultured in an incubator of 37° C. and 5% $CO_2$ for 24 h until the cells adhered to the wall of the 96-well plate. Three groups of drug solutions with concentration gradients were added (ZnHgSe quantum dot gradient: 2400 μg·mL$^{-1}$, 1200 μg·mL$^{-1}$, 600 μg mL$^{-1}$, 300 μg·mL$^{-1}$, 150 μg·mL$^{-1}$, and 75 μg·mL$^{-1}$; DMF gradient: 800 μg mL$^{-1}$, 400 μg·mL$^{-1}$, 200 μg·mL$^{-1}$, 100 μg·mL$^{-1}$, 50 μg·mL$^{-1}$, and 25 μg·mL$^{-1}$; corresponding DMF-QD gradient was determined according to DMF concentration by equivalent conversion). Each group was repeated with 6 wells, with an additional zero-adjustment well and a control well. After incubation for 24 h at 37° C. in a 5% CO$_2$ atmosphere, 20 μL of 5 mg·mL$^{-1}$ MTT solution was added to each well, and the cells were incubated with 100 μL of the culture medium. After incubation for 4 h, the culture medium was discarded, followed by addition of 150 μL of DMSO, and the cells were placed on a shaking table at low speed for 10 min. The absorbance value OD of each well was measured by an enzyme-linked immunosorbent detector at a wavelength of 490 nm, and the cell growth inhibition rate (IC$_{50}$) was calculated. IC$_{50}$ value was calculated according to the modified Karber's method:

$$\lg IC_{50} IC_{50} = X_m - I \times \left(P - \frac{3 - P_m - P_n}{4}\right)$$

where: $X_m$, I, P, $P_m$, and $P_n$ refer to the maximum lg dose value, Ig (maximum dose/adjacent dose) value, the sum of positive response rates, the maximum positive response rate, and the minimum positive response rate, respectively. The test results were shown in Table 1.

TABLE 1

IC$_{50}$ values of different drugs on human gastric cancer MGC-803 cells (n = 6, $\overline{X}$ ± SD)

| Drugs | ZnHgSe | DMF | DMF-QD |
|---|---|---|---|
| IC$_{50}$(μg · mL$^{-1}$) | 552 ± 43.18 | 218 ± 11.47 | 191 ± 10.03 |

Physicochemical Properties of DMF-QD Nanoparticle and its Role in Inducing Nuclear Explosion of Cancer Cell.

Figure 1:
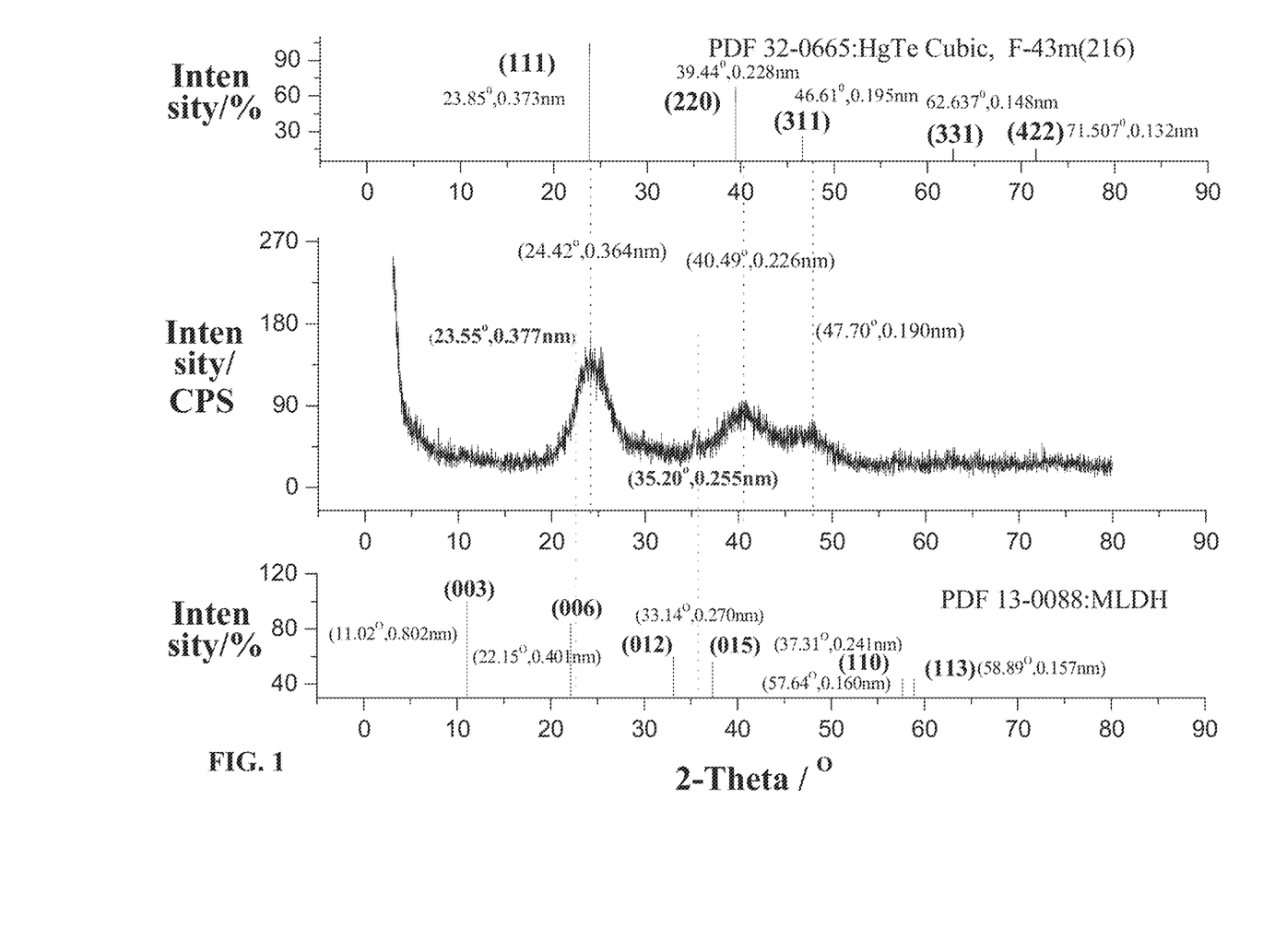
FIG. 1 is an X-ray diffraction (XRD) result of DMF-QD nanoparticle.

(1) Phase Analysis and Physicochemical Properties of DMF-QD Nanoparticle:

FIG. 1 was an X-ray diffraction (XRD) result of the DMF-QD nanoparticle and JCPDS standard cards such as 32-0665 and 13-0088 used for identification. 32-0665 was the standard pattern of cubic sphalerite crystal form, and 13-0088 represents the XRD characteristic of the L-layered crystal of R-hexagonal system Fe$_{3.6}$Fe$_{0.9}$(O, OH, Cl)$_9$, which was an important basis for DMF identification. ZnHgSe-DMF nanoparticle showed relatively obvious diffraction peaks of quantum dots, but diffraction peak of magnetic layered double hydroxide (MLDH) was not prominent, and only weak diffraction of (006) (23.55°, 0.377 nm) was observed. Because the DMF-QD nanoparticle used for characterization was taken from Example 1, the mass ratio of the quantum dots to DMF in the preparation raw material was 3:1, and the proportion of DMF was too small (the MLDH diffraction of the DMF-QD nanoparticle prepared in Example 2 and Example 3 was enhanced). Due to the organic combination of dextran on the surface layer and the intercalation of quantum dots on the outer layer, the MLDH crystal phase was masked. ZnHgSe-DMF nanoparticle exhibited crystalline phase of ZnHgSe and part of MLDH, which meant the embedding and grafting of the quantum dots on the DMF surface was successful.

Figure 2:
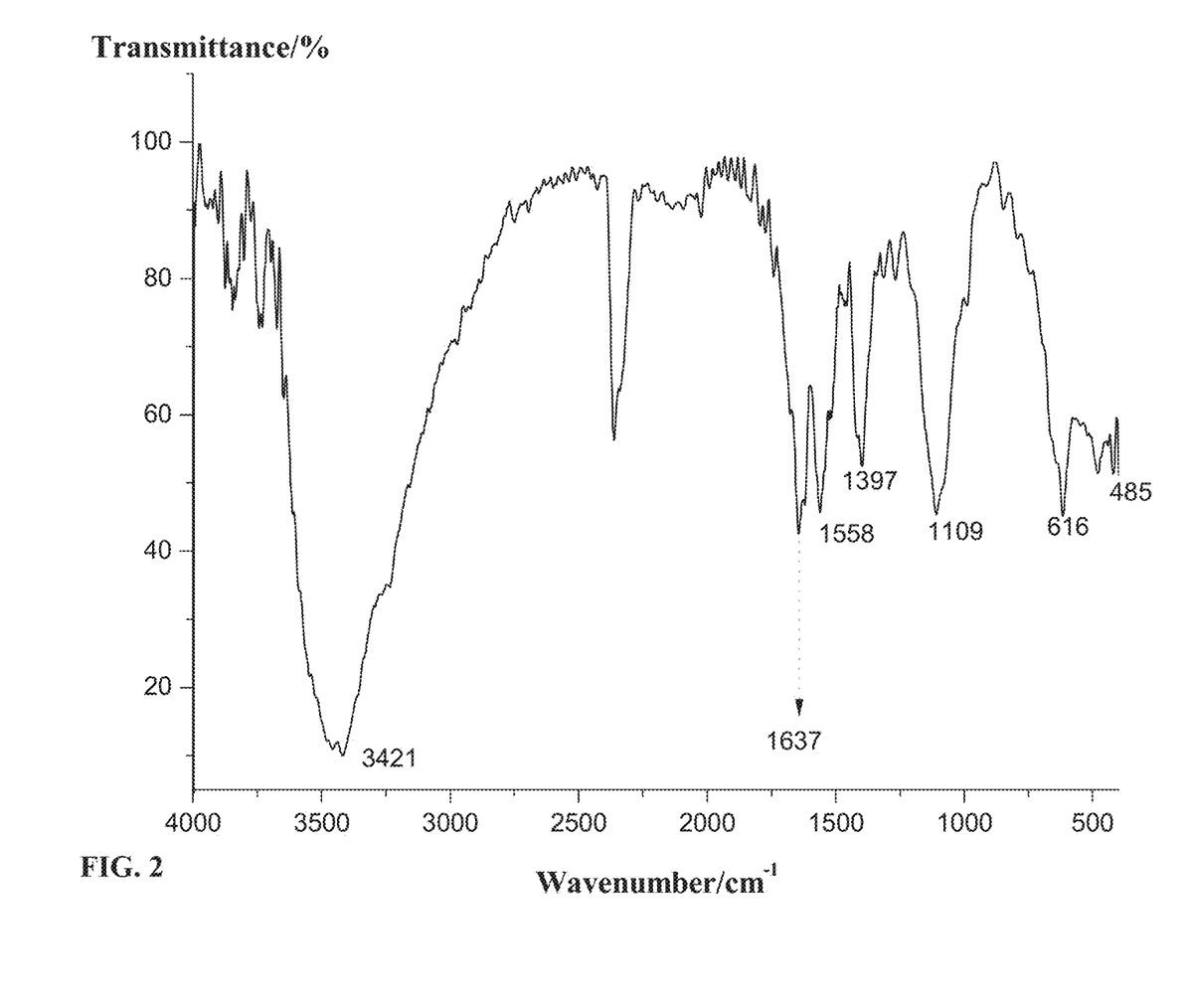
FIG. 2 is a Fourier-transform infrared spectroscopy (FT-IR) spectra of DMF-QD nanoparticle.

FIG. 2 was a Fourier-transform infrared spectroscopy (FT-IR) spectra of DMF-QD nanoparticle. IR absorption of ZnHgSe quantum dots was detected at the marked positions of 3413, 1647 and 1558 cm$^{-1}$. The stretching vibration peak of hydroxyl of the DMF was red shifted from 3413 cm$^{-1}$ to 3421 cm$^{-1}$, and the stretching vibration peak $V_{C=O}$ of carboxyl of the quantum dot ligand was blue shifted from 1647 cm$^{-1}$ to 1637 cm$^{-1}$, and the peak area at 1558 cm$^{-1}$ became smaller, which illustrated that some of the quantum dots and the DMF may undergo condensation reactions of carboxylic group with hydroxyl group. The absorption at 1109 cm$^{-1}$ was the red shift at 1013 cm$^{-1}$ of DMF, which corresponds to the $V_{C-OH}$ vibration mode (1160-1013 cm$^{-1}$) of the dextran on the surface of DMF. The IR absorptions occurred at 616 cm$^{-1}$ and 485 cm$^{-1}$ were stretching vibrations $V_{M-O}$ of the laminate lattice oxygen in the DMF. IR analysis obtained the information including coexistence of multifunctional groups in the sample and the combination of quantum dots and DMF.

Figure 3A:
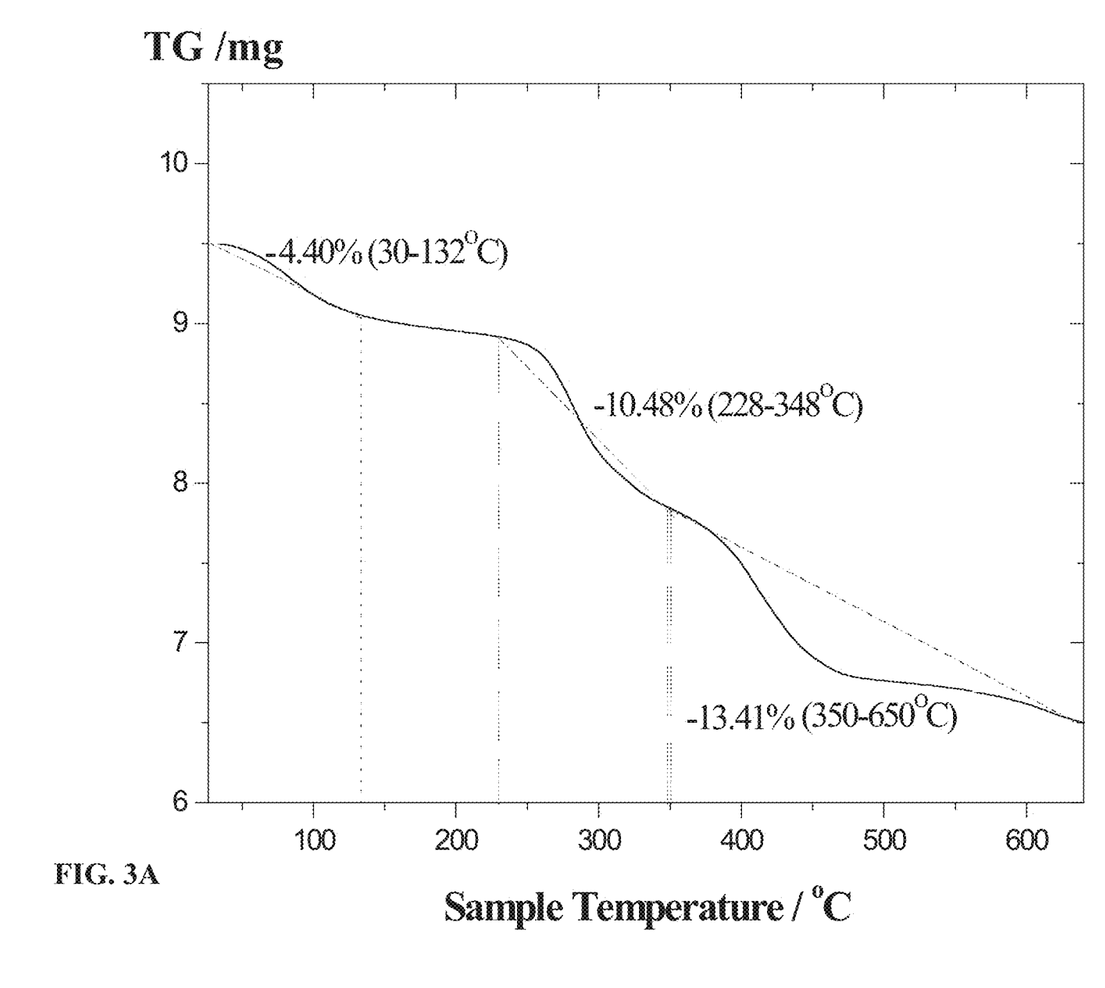
FIGS. 3A-3B are experimental results of thermogravimetry analysis (TG) for characterizing DMF-QD nanoparticles.
Figure 3B:
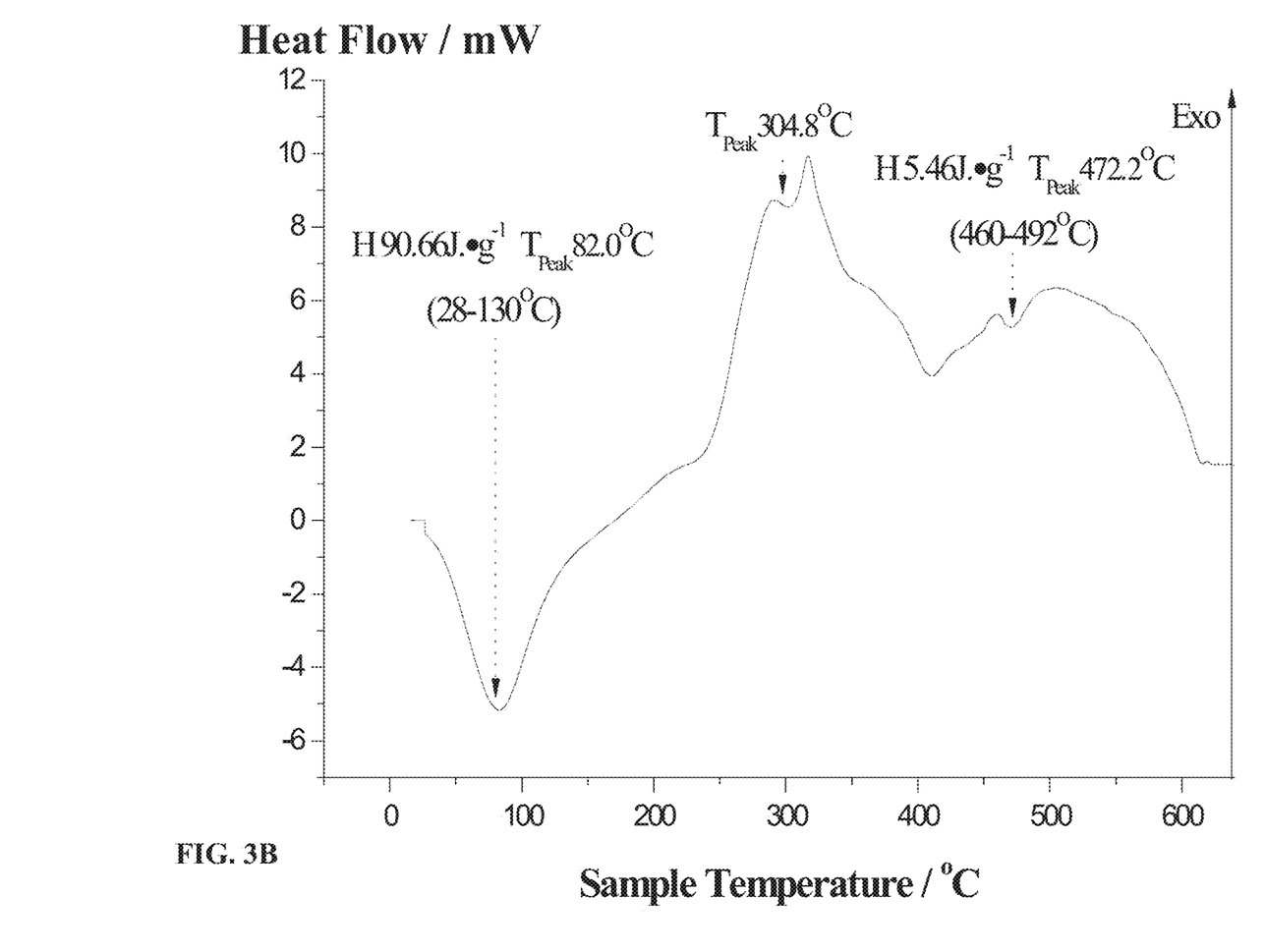

FIGS. 3A-3B showed a heat flow curve and a TG curve of DMF-QD nanoparticle. The TG curve indicated that the thermal decomposition of the DMF-QD nanoparticle was accompanied by three weight loss process, in which the first weight loss was about 4.4%, corresponding to an enthalpy of 90.66 J·g$^{-1}$, in the temperature region of 30-132° C. and being a dehydration weight loss. The second weight loss was about 10.48% in the temperature region of 228-348° C. The differential scanning calorimetry (DSC) curve for the exothermic process was divided into two stages with a boundary of 304.8° C. The exothermic process was related to the decomposition of the quantum dot ligand MPA, and to the decomposition of the organic components FU and DET in the DMF. Two endothermic decompositions occurred after 350° C., which was related to the disintegration of the quantum dot architecture. The total weight loss was about 13.41% in the temperature region of 350-650° C. The reasons for the third weight loss include the endothermic decomposition of the quantum dot architecture, the endothermic decomposition of the MLDH layer of the DMF, and the endothermic decomposition of the LDO-Organics complex (corresponding to an endothermic enthalpy of 5.46 J·g$^{-1}$ in the temperature region of 460-492° C.). The exothermic process was related to the recombination and deep decomposition of the remaining quantum dots and DMF.

Figure 4:
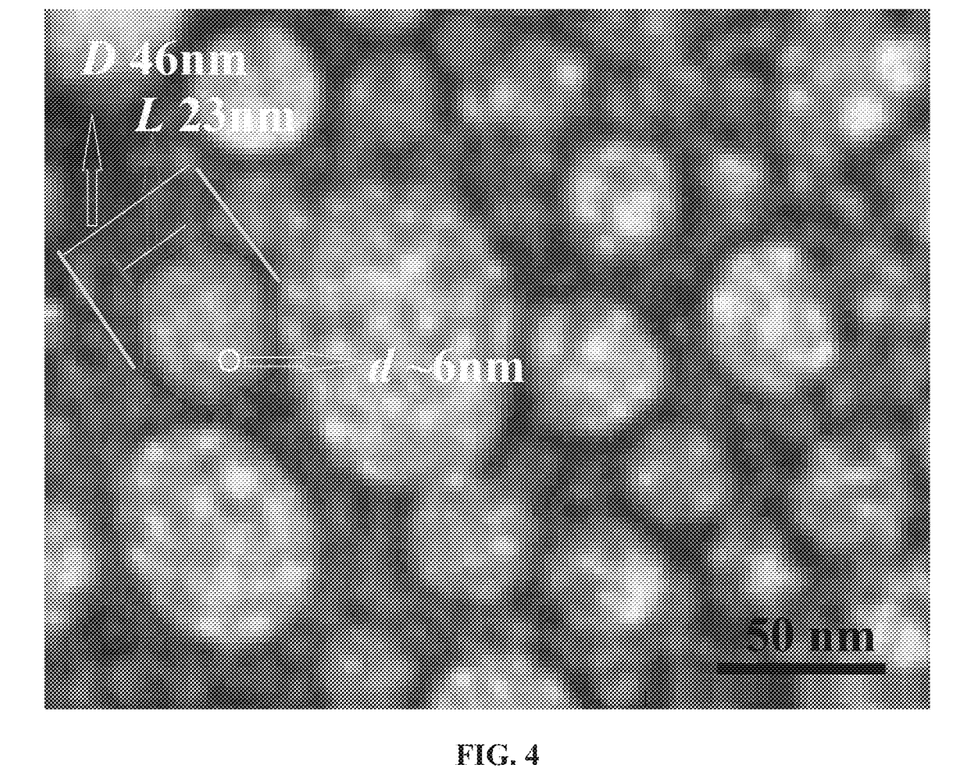
FIG. 4 is a morphology of DMF-QD nanoparticles by a transmission electron microscope (TEM)

FIG. 4 was a morphology of DMF-QD nanoparticles prepared in Example 2 by a transmission electron microscope (TEM). The DMF-QD nanoparticles were in a condensed state, with tight agglomeration and low dispersion, but the morphology of the frame particles and the chimeric state of the quantum dots were clearly visible. The frame particles were different in their size, with a diameter between 30 and 100 nm, and had a hexagonal-layered appearance, most of which were oval spheres. The marked frame particle had a hexagonal base frame with a side length of 23 nm and a diameter of about 46 nm, which can represent the average level of different nanoparticles in the figure. The quantum dots were uniformly embedded and bonded on the surface of the base frame of the DMF, exhibiting an embedded bonding characteristic. The electrostatic binding tendency of quantum dots to MLDH laminates was obvious. Quantum dots had a diameter of about 6 nm and were in a multi-quantum dot cluster state. TEM image provided the visual evidence that the nanoscale quantum dots and the DMF particles had been assembled to form the DMF-QD nanoparticles.

Figure 5:
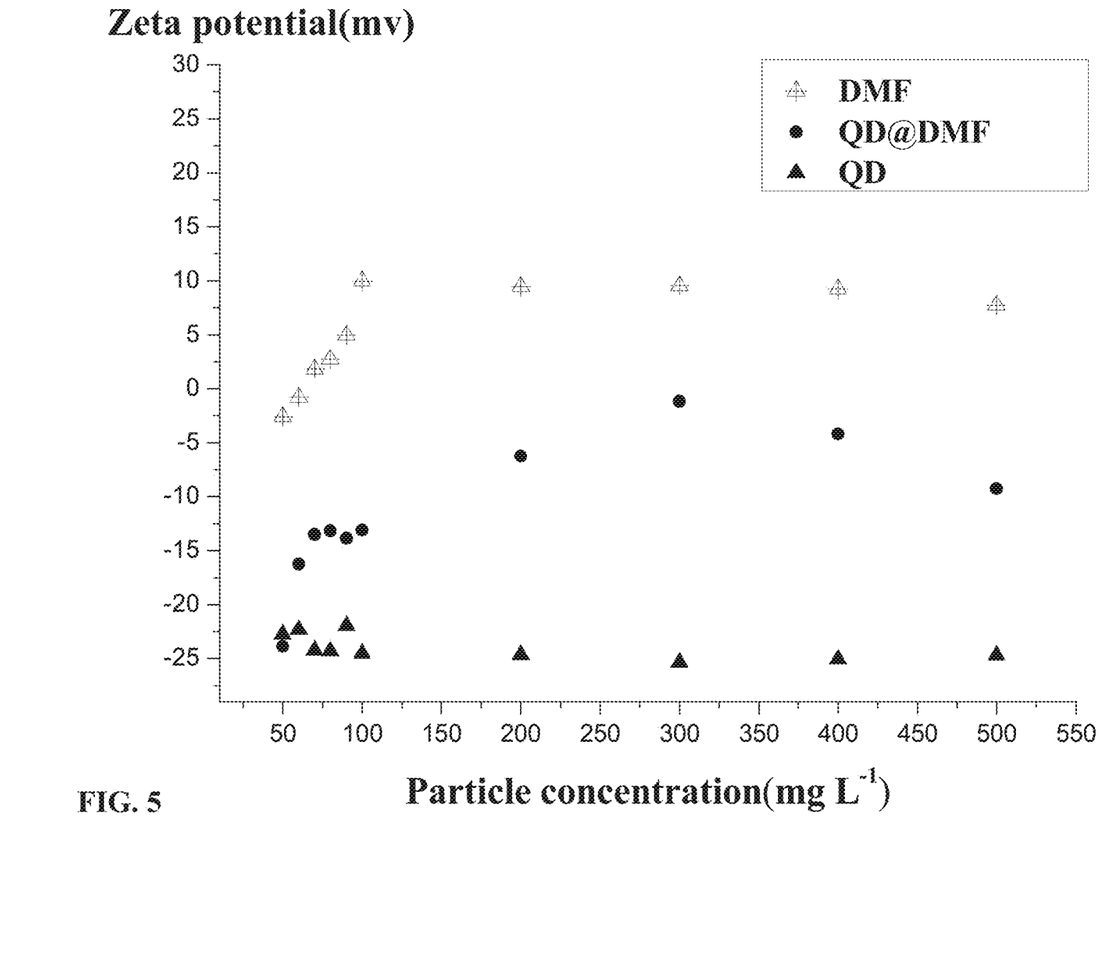
FIG. 5 is a zeta potential and its changes of DMF-QD nanoparticles.

Zeta potential had an effect on the biological transport and application performance of samples. The samples prepared in Example 2 were used as a test object to measure the zeta potential of the ZnHgSe quantum dot. DMF particle, and DMF-QD nanoparticle, and analyze their changes with concentration. The results were shown in FIG. 5. The zeta potential of the quantum dots was basically unchanged in the neutral solution. The zeta potential of the DMF and the DMF-QD changed significantly with particle concentration from 50 mg·$L^{-1}$ to 500 mg·$L^{-1}$, in which the zeta potential of the DMF increased from −2 mV to 9 mV, and then remained unchanged after 200 mg·$L^{-1}$. The DMF-QD nanoparticle changed parabolically (converted to a negative value) with the increasing concentration of particle. The zeta potential of DMF-QD nanoparticle increased from −23.87 mV to −13.5 mV, when the particle concentration increased from 50 mg·$L^{-1}$ to 70 mg·$L^{-1}$. Then the zeta potential of DMF-QD remained at about −13.5 mV in the concentration region of 70 mg·$L^{-1}$ to 100 mg·$L^{-1}$. The zeta potential moved in the direction of increasing negative value after the concentration reached about 300 mg·$L^{-1}$. Quantum dot and DMF particle exhibited colloidal stability in different potential ranges. The potential of the DMF-QD nanoparticle was between the potential of the quantum dots and DMF particles, with a sufficient colloidal stability in the concentration range far from 300 mg·$L^{-1}$.

Figure 6:
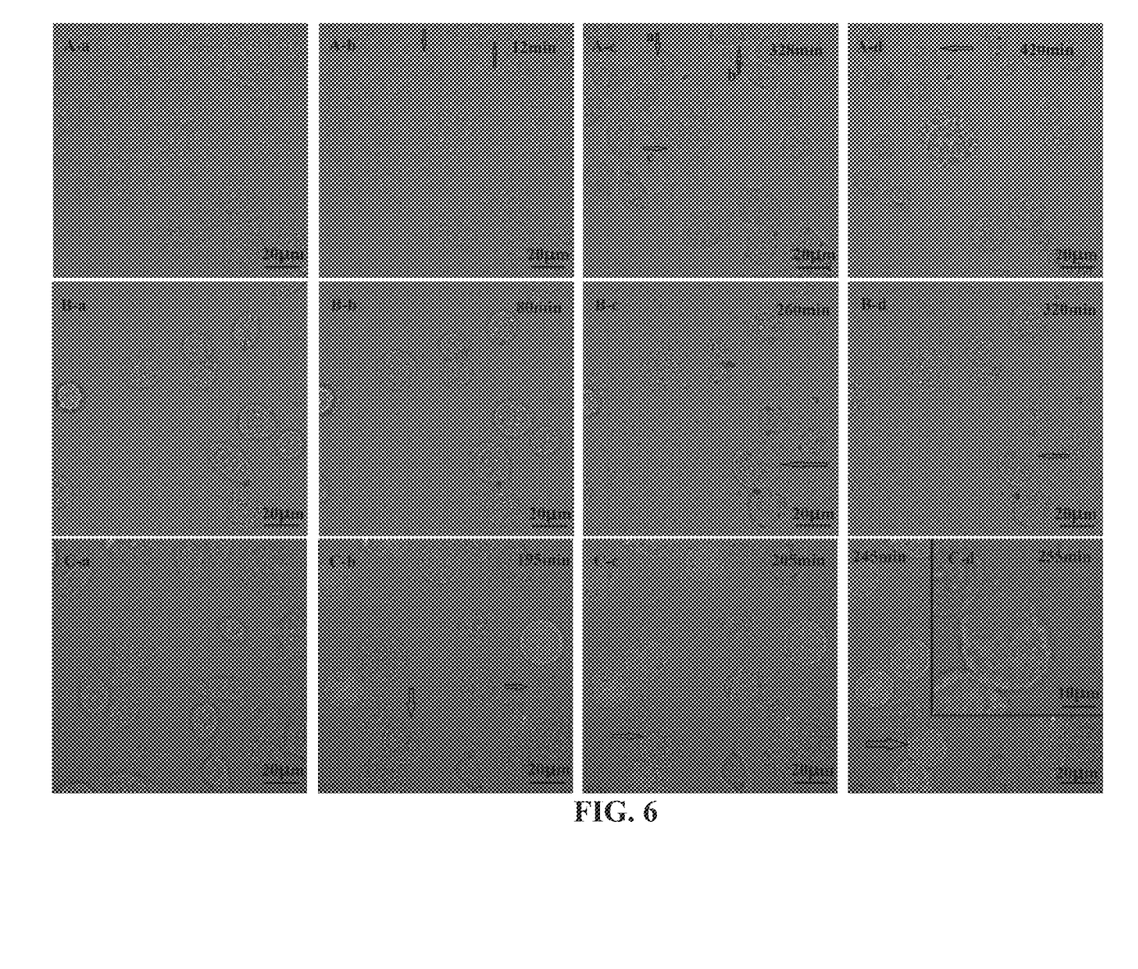
FIG. 6 is a live cell imaging result of human gastric cancer MGC-803 cells incubated with DMF-QD nanoparticles having a concentration of 1.4 mg/μL for 7 h.

(2) In Situ Imaging Results of Nuclear Explosion of Human Gastric Cancer MGC-803 Cells Caused by DMF-QD Nanoparticles FIG. 6 showed the real-time imaging results of live cells during the interaction of ZnHgSe quantum dot, DMF and DMF-QD particles with human gastric cancer MGC-803 cells. The picture A-a in FIG. 6 showed that in the initial period of application of pure quantum dots, the cells grew normally and the quantum dots could not invade cells on a large scale. After action for 12 min, the quantum dots moved between the cancer cells. Some quantum dots (indicated by arrows) adhered to the plasma membrane of the cell and emit weak red fluorescence, but most cells had normal morphology and in an active status. After action for 328 min, quantum dots appeared in the cytoplasm of some cancer cells, but the cells maintained the normal morphology and the vitality such as rejection and movement (picture A-c in FIG. 6). After action for 420 min, the cancer cells showed a toxic response to the quantum dots. Many cells tend to be round (the total volume exhibited shrinkage), and the cell body also exhibited shrinkage, showing the phenomenon of cancer cells rejecting quantum dots and extruding cell body from the cytoplasm (picture A-d in FIG. 6). The above phenomenon indicated that the cell had a weak affinity, a strong rejection, and a tolerance for a long time for the pure quantum dots. Quantum dots only cause the morphological changes of the cell body, and cannot cause the nucleus to explode.

DMF particles interacted with cells quickly and strongly. DMF particles quickly triggered cellular defense mechanism and rejection reaction when initially contacting with cancer cells, that is: the black particle flow can move around the outer periphery of the cell body; the black particles were discharged from the membrane vent or moved between the cancer cells, illustrating that the DMF particles can quickly enter the cell body to trigger the intracellular responses and have a strong affinity for the cell membrane. The organelles were in an active state of motion and the cells maintained their normal shape (picture B-a in FIG. 6). After action for 80 min, the cells still retained the ability to reject and defend against DMF particles. At the same time the DMF particles entering the cell body in the early stage had caused a toxic reaction inside the cytoplasm-organelles, that is: organelles, nuclei and nucleoli swelled, and the nucleus and cell body were rounded (picture B-b in FIG. 6). After action for 260 min, the cell rejection reaction became more intensive. The number of black particles discharged by the cancer cells increased. The exocytosis and endocytosis of the cancer cells and the particle activity in the cytoplasm were in an abnormally active state. The cytoplasm of a cell indicated by an arrow was extremely swollen, and black particle flow can be observed on the inner periphery of the nuclear membrane and the outer periphery of the nucleoli (picture B-c in FIG. 6). After another 1 h (action for 320 min), the cell indicated by the arrow (the cell that swelled to the limit in the previous figure) exploded from the edge of the nucleus, and then the cell body on the right ruptured completely, and all the serous fluid leaked out of the cells. Other cancer cells also began to swell sharply, and some continued to maintain rejection reaction.

The picture C-a in FIG. 6 showed that DMF-QD particles rapidly caused the cell swelling leading to cell death, and red fluorescent particles appeared in the plasma membrane and the nucleus of individual cells in the early stage of imaging (about 10-15 min after dosing). Most of the cells have normal morphology and good survival status although the cancer cells exhibited defensive behavior. After action for 195 min, about 50% of the cells began to explode, expanding from the nucleus to the boundary of the membrane. As shown in FIG. 4, the cell membrane indicated by an arrow bulged outward and eventually formed a vesicle without organelles, showing a significant change in cell membrane permeability before the nucleus explodes. After another 10 min (action for 205 min), more cells swelled, and the nucleus of the middle right cell collapsed, and the cell body were fragmented, and the nucleoli emitted a strong red fluorescence. As shown in the picture C-c in FIG. 6, the DMF-QD nanoparticle outside the cell indicated by an arrow rapidly passed through the cell membrane and entered the cytoplasm, indicating that the cell body swelling and intensified cell membrane permeability were simultaneous processes. After another 30 min (action for 245 min), the cell eventually exploded and thus caused red fluorescence throughout the cell, indicating that the cytoplasm and nucleus already contained a large number of DMF-QD particles. As shown in the picture C-c in FIG. 6, after 255 min, the cell nucleus dissolved and exploded, and the resulted shock wave broke through the entire cell, causing the membrane to rupture and the serous fluid with red fluorescence to flow out of the cell.

Figure 7:
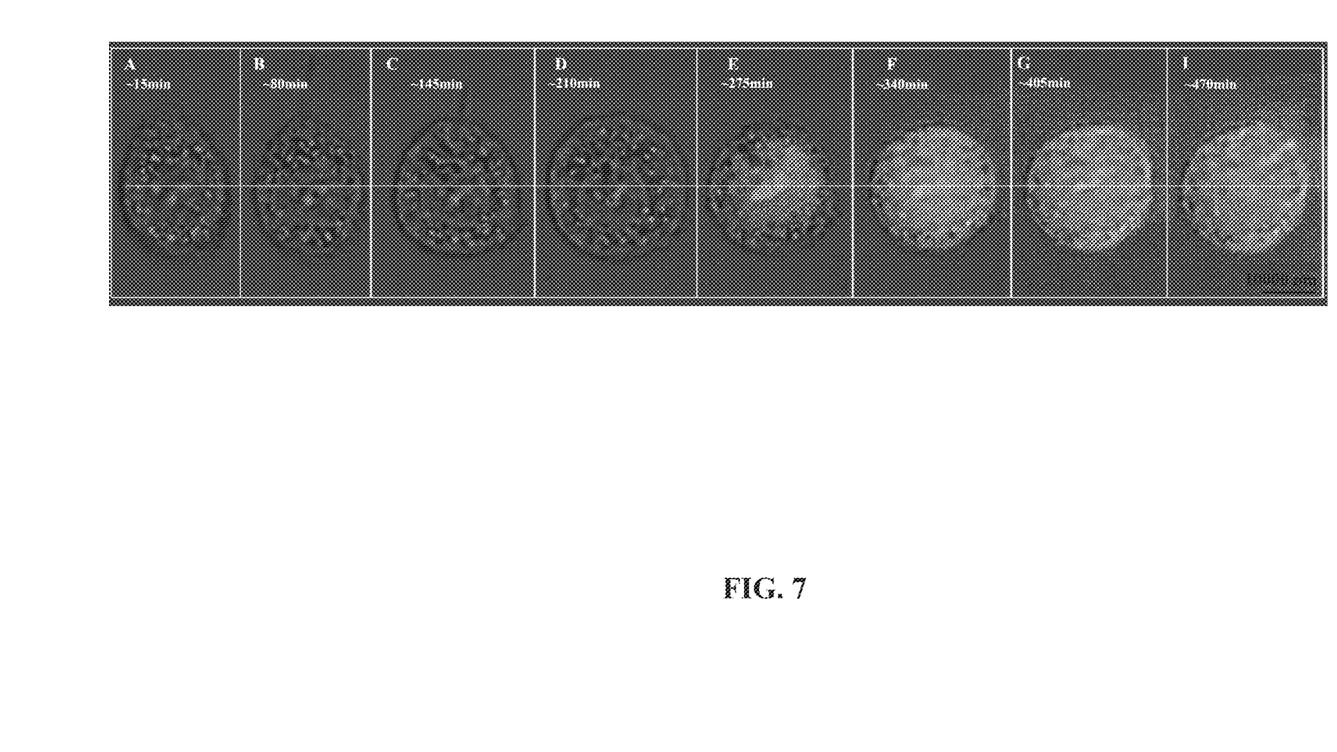
FIG. 7 is a live cell imaging result of human gastric cancer MGC-803 cells incubated with DMF-QD nanoparticles having a concentration of 1.2 mg/μL for 7 h.
Figure 8:
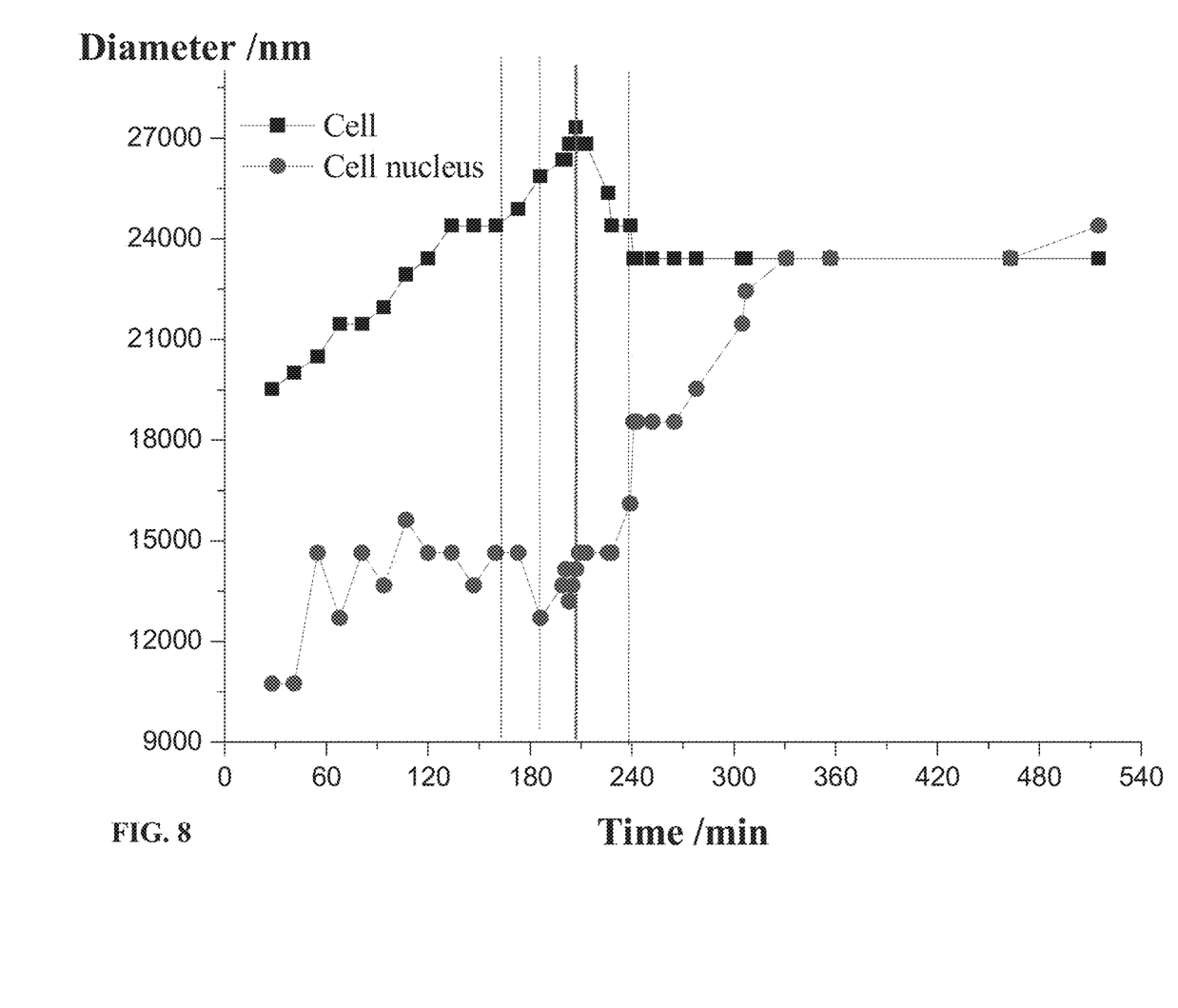
FIG. 8 is a curve of the diameter of the nucleus and the cell body of human gastric cancer MGC-803 cells during the cell swelling and death.

FIG. 7 showed the imaging results of a process of tracking nanoparticles in Example 3 that triggered the swelling of a single cancer cell until the nuclear explosion. The eight images proved that the test cancer cells undergone six different stages of endocytosis, exocytosis, cell body expansion, nucleus lysis, nuclear explosion, and cell breakdown. The pictures A and B in FIG. 7 showed that the DMF-QD nanoparticles could complete the internalization by cancer cells and entered the cytoplasm within 15 minutes. The cancer cells immediately respond to the continuous internalization of the particles with defensive reaction and exocytosis behavior. After action for 80 min, the cells still maintained normal physiological responses such as exocytosis, but the nucleus had exhibited dramatically swelling, illustrating that the DMF-QD nanoparticles had entered the nucleus and thus caused strong pharmacological and somatic stress responses. The degree of swelling of organelles and cell body continued to increase in the period of 145 to 275 min. After that, the nucleus burst and the contents of the nucleus were sprayed from the inside to the outside, further breaking through the bondage of the cell membrane. During the period of 340 to 470 min, the magnitude of the explosion and spray of the nucleus continued to expand. After action for 470 min, the nucleus almost completely exploded out of the membrane vent, and the cell contents and organelles also leaked. Eventually, the cell body disintegrated, swelled and died. FIG. 8 was a curve of the diameter of the nucleus and the cell body of the human gastric cancer MGC-803 cells during the cell swelling and death. There were 3 important time nodes on the image. With the first time point of 170 min as a boundary, the cell body continued to swell to a plateau, and then expanded again and reached the maximum volume at 192 min, after which it quickly contracted. The settings were maintained from 240 min until the end of the nuclear explosion. The nucleus diameter was maintained nearly constant for the first 30 min, and increased by approximately ±1220 nm in the period of 50 to 239 min, reflecting the active physiological reactions such as deformation and contraction and expansion of the nucleus during the interaction between cancer cells and DMF-QD nanoparticles. With the second time point of 239 min as a boundary, after the nucleus completed the last contraction and deformation within a very short time interval (about 60 s), the nucleus immediately began to explode dramatically and the volume of the nucleus increases rapidly. After maintaining a plateau of about 30 min, the nucleus continued to swell until the cell body disintegrated and the nuclear explosion ended.

(3) MTT results of DMF-QD nanoparticles on human gastric cancer cell MGC-803. MTT experiments showed that the cell proliferation inhibition rate increased with increasing sample concentration after quantum dots, DMF particles, and DMF-QD nanoparticles respectively interacted with human gastric cancer MGC-803 cells for 24 h. The result showed a dose-response relationship and a significant statistical difference (P<0.01). DMF-QD had a higher cell proliferation inhibition rate than ZnHgSe quantum dot and DMF, after the quantum dots, DMF particles and DMF-QD nanoparticles at the same concentration were respectively treated with cancer cells for the same time. The results showed that a smaller dose of DMF-QD nanoparticles achieved good efficacy in clinical trials. The $IC_{50}$ value of each sample on human gastric MGC-803 cells was calculated according to the modified Karber's method (Table 1): ZnHgSe quantum dot had the largest $IC_{50}$ value, indicating ZnHgSe quantum dot had relatively low toxicity than DMF and DMF-QD, while the cytotoxicity per unit mass of DMF was about 2.6 times that of quantum dots. The cytotoxicity per unit mass of DMF was approximately 2.6 times that of quantum dots. The cancer cell toxicity of DMF was related to the system loading and release of anti-tumor drugs, and the MLDH carrier may also have certain effects on specific organelles. But the main reason was that DMF had a strong cell transport capacity and nuclear targeting performance, which was convenient for the carried drug MLDH to have the most direct killing effect on cancer cells, and the cytotoxicity of quantum dots only was related to its metal ion toxicity. The $IC_{50}$ value of DMF-QD was the smallest, illustrating the strongest toxicity to cancer cells and showing the additive effect of nano-drugs and quantum dots. That is, ZnHgSe quantum dots bound to the surface of DMF caused toxic damage to cancer cells by releasing $Hg^{2+}$ when the stabilizer mercaptopropionic acid falls off. Therefore, the cancer cell toxicity caused by the complex was related to actual intake of DMF drugs and quantum dots, and intracellular metabolism.

The above cell biology experiments showed that the pure quantum dots have low toxicity to cancer cells, and the resulting cancer cell changes were limited to the weakening of proliferative activity, while leaving the structure of organelles such as cell membrane and nucleus intact. The organelles swelled and the membrane ruptured when DMF particles acted on cells. The morphological change process of cancer cells caused by DMF-QD nanoparticles with quantum dots as a fluorescent marker can be displayed very clearly and completely. The nuclear explosion process of cancer cells included swelling and expansion of the nucleus, which pushed the cytoplasm until it breaks through the entire cell. The nuclear explosion was the result from the assembled action of all the composite components of the DMF-QD nanoparticle. Quantum dots did not have obvious cytotoxic effect on cells, and did not possess the advantages of cell fusion and transport. However, the electrostatic binding of quantum dots and DMF further strengthened the ability of DMF particles to kill cancer cells in a swelling and death manner, with a superimposing effect. The fusion of quantum dots significantly strengthened the damage of DMF particles to organelles, especially to the damage to nucleus, and the intensity of energy bursts. The above results showed that DMF-QD nanoparticles had great application prospects in clinical treatment, biological imaging, and research on cell swelling mechanism leading to death.

It will be obvious to those skilled in the art that changes and modifications may be made, and therefore, the aim in the appended claims is to cover all such changes and modifications.

What is claimed is:

1. A method, comprising:
   a) dissolving $Zn(NO_3)_2$ in water thereby yielding a $Zn(NO_3)_2$ solution, deaerating the $Zn(NO_3)_2$ solution using magnetic stirring under nitrogen atmosphere at room temperature; adding $Hg(NO_3)_2$ solution to the $Zn(NO_3)_2$ solution at a molar ratio of $Zn^{2+}/Hg^{2+}$ from 1:0.03 to 1:0.06 thereby yielding a first dispersion, and adding a mercaptopropionic acid solution to the first dispersion at a molar ratio of $Zn^{2+}$/mercaptopropionic acid from 1:1.6 to 1:2.0 thereby yielding a second dispersion; and adjusting the pH of the second dispersion to 6.0-9.0 thereby yielding a precursor solution comprising $Zn^{2+}$—$Hg^{2+}$-mercaptopropionic acid;
   b) adding a selenium (Se) powder and a $NaBH_4$ solid at a molar ratio of $Se/NaBH_4$ from 1:1.5 to 1:2.5 in water thereby yielding a reaction mixture; magnetically stirring the reaction mixture at a constant temperature of 40-50° C. under nitrogen atmosphere thereby yielding a NaHSe slurry;
   c) mixing the precursor solution comprising $Zn^{2+}$—$Hg^{2+}$-mercaptopropionic acid and the NaHSe slurry at a molar ratio of $Zn^{2+}$/NaHSe from 1:0.125 to 1:1 thereby yielding a first mixture; stirring the first mixture using magnetic stirring at a constant temperature of 80-100° C. under nitrogen atmosphere thereby yielding a mixed slurry;
   d) aging the mixed slurry; adding ethanol to the mixed slurry thereby yielding a supernatant and a precipitate; discarding the supernatant, and centrifuging the precipitate to obtain a solid-phase sample; washing the solid-phase sample with absolute ethanol and drying under vacuum, thereby yielding ZnHgSe guantum dots;
   e) preparing a drug delivery system comprising dextran-magnetic layered double hydroxide-fluorouracil (DMF); blending and grinding the drug delivery system and the ZnHgSe quantum dots at a mass ratio from 1:1 to 1:3 thereby yielding a mixed powders; and
   f) dispersing the mixed powders obtained in e) in absolute ethyl alcohol thereby yielding a first suspension; ultrasonicating the first suspension thereby yielding a second suspension, separating the second suspension into a solid product and a liquid product using magnetic separation method; centrifuging and washing the solid product using absolute ethyl alcohol, and vacuum drying, wherein the solid product is a magnetic layered fluorescent nanoparticle comprising fluorouracil and ZnHgSe quantum dots.

2. The method of claim 1, wherein in a), deaerating the $Zn(NO_3)_2$ solution is implemented for 30-40 min; the mercaptopropionic acid solution is mixed with the dispersion for 30-60 min, and the pH of the second dispersion is adjusted to 6.0-9.0 using a 2.0 mol×$L^{-1}$ NaOH solution.

3. The method of claim 1, wherein in d), the mixed slurry is aged for 40-80 min; the solid-phase sample is washed with absolute ethanol for 2-3 times; centrifuging the precipitate to obtain a solid-phase sample is carried out at 4000-5000 rpm and 20° C.; the solid-phase sample is dried at 65-80° C. under 0.085 megapascal; and in a) and c), the magnetic stirring is performed at 200-300 rpm.

4. The method of claim 1, wherein in f), the first suspension is ultrasonicated in a 30-50° C. water bath for 1-3 hours.

5. The method of claim 1, wherein in f), the solid product is washed using absolute ethyl alcohol for 2-3 times.

6. The method of claim 1, wherein in f), the solid product is dried at 50-60° C. under 0.085 megapascal.

* * * * *